United States Patent [19]

Ward et al.

[11] 4,293,722

[45] Oct. 6, 1981

[54] PROCESS FOR CONVERSION OF PROPANE TO GASOLINE

[75] Inventors: Dennis J. Ward, South Barrington; Bipin V. Vora, Elk Grove Village, both of Ill.

[73] Assignee: UOP Inc., Des Plaines, Ill.

[21] Appl. No.: 121,353

[22] Filed: Feb. 14, 1980

[51] Int. Cl.³ .......................... C07C 2/08; C07C 5/32
[52] U.S. Cl. .................................. 585/330; 585/314; 585/315; 585/520; 585/654; 585/721
[58] Field of Search ............... 585/330, 654, 520, 721, 585/314, 315

[56] References Cited

U.S. PATENT DOCUMENTS 2,456,672 12/1948 Bloch et al. ........................ 585/314

*Primary Examiner*—Curtis R. Davis
*Attorney, Agent, or Firm*—James R. Hoatson, Jr.; John F. Spears, Jr.; William H. Page, II

[57] ABSTRACT

A multi-step hydrocarbon conversion process for producing gasoline from propane is disclosed. Propane is passed into a dehydrogenation zone and the entire dehydrogenation zone effluent is then passed into a catalytic condensation zone wherein propylene is converted into $C_6$ and $C_9$ hydrocarbons. The condensation zone effluent, a stripper overhead stream and an absorber bottoms stream are commingled and then separated into vapor and liquid portions. The liquid is passed into the stripper, and the vapor portion is contacted with stripper bottoms liquid in an absorber. The absorber overhead stream is contacted with liquid propane in a second absorber to remove $C_6$ hydrocarbons and is then recycled to the dehydrogenation zone. Depropanizing a portion of the stripper bottoms yields the liquid propane and a gasoline product.

4 Claims, 1 Drawing Figure

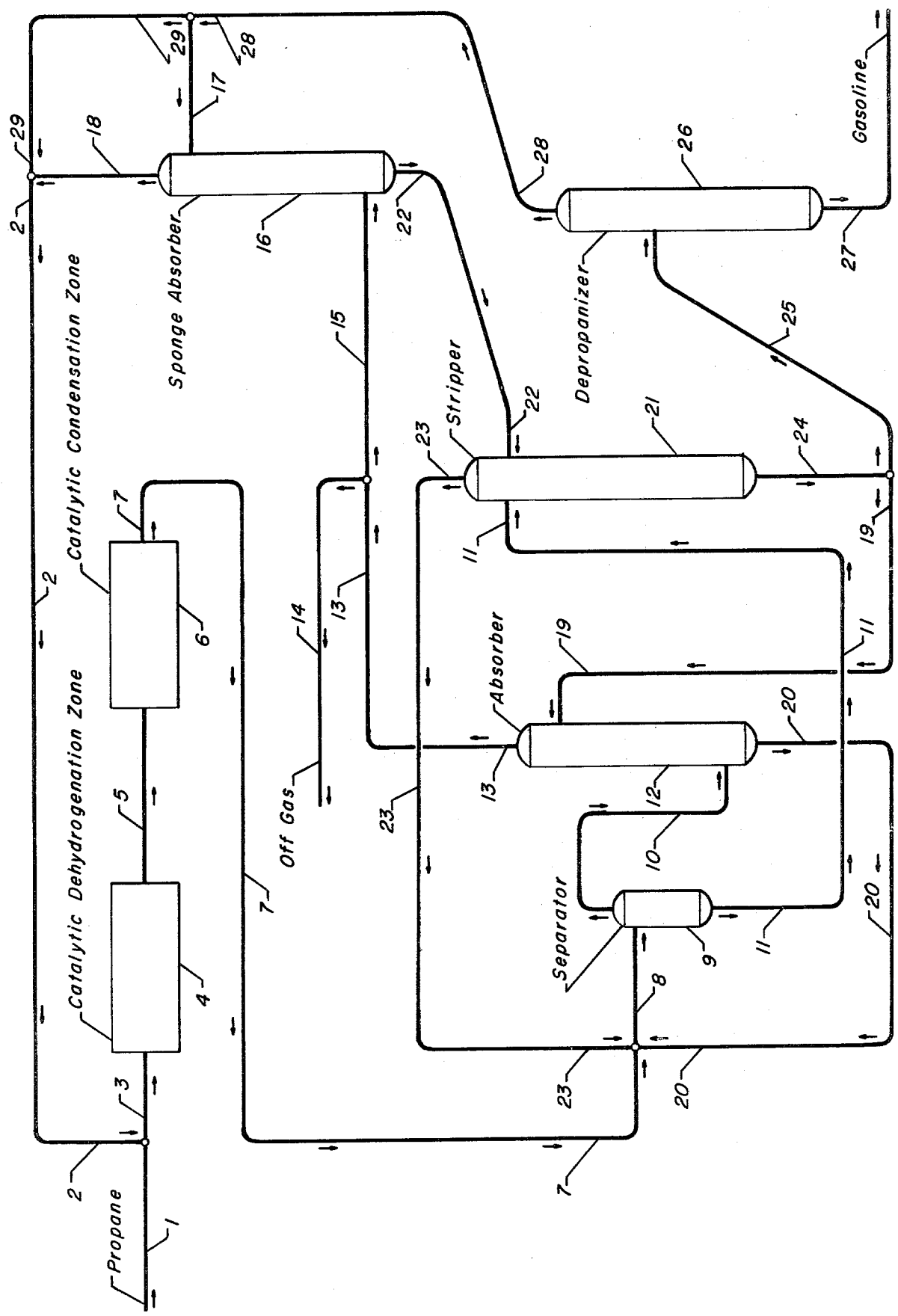

PROCESS FOR CONVERSION OF PROPANE TO GASOLINE

FIELD OF THE INVENTION

The invention is a novel integrated hydrocarbon conversion process for producing gasoline from propane. The invention relates to such processes as the dehydrogenation of light normal paraffins and the catalytic condensation (oligomerization) of propylene. The invention also relates to processes for the separation and recovery of light hydrocarbons through the use of absorption and stripping columns similar to those used in the gas concentration units of catalytic cracking units. The invention therefore relates to processes similar in nature to those described in U.S. patents classified in Classes 208, 210 and 585 (previously Cl. 260–666 et.-seq.).

PRIOR ART

Catalytic processes for the dehydrogenation of light paraffins and for the catalytic condensation of light olefins to produce gasoline boiling range hydrocarbons are well known. The use of an absorption column and stripping column fed from a vapor-liquid separator to recover light hydrocarbons is also well known and is widely practiced.

Processes for the dehydrogenation of light normal paraffins are described in U.S. Pat. Nos. 3,391,218 (Cl. 260–683.3); 3,448,165 (Cl. 260–683.3); 3,647,719 (Cl. 252–466PT); 3,649,566 (Cl. 252–470); 3,647,911 (Cl. 260–683.3); 3,714,281 (Cl. 260–668D); 3,742,078 (Cl. 260–668D); and 3,755,481 (Cl. 260–668D). These references describe the catalysts and process conditions which may be employed. The preferred dehydrogenation catalyst is described in U.S. Pat. No. 3,745,112 (Cl. 208–139).

Processes for the catalytic condensation (oligomerization) of light olefins using a heterogeneous catalyst are described in U.S. Pat. Nos. 3,916,019 (Cl. 260–683.15E); 3,959,400 (Cl. 260–683.15R); 4,098,839 (Cl. 260–683.15D) and 4,113,790 (Cl. 260–683.15B). Process flow diagrams for oligomerization processes which utilize a solid phosphoric acid (SPA) catalyst are presented in U.S. Pat. Nos. 3,437,706; 3,437,707; 3,437,708; and 3,510,534 (all Cl. 260–671).

Solid phosphoric acid catalysts are described in U.S. Pat. Nos. 3,050,472; 3,050,473; 3,132,109 (all Cl. 252–435) and 3,402,130 (Cl. 252–437).

The simultaneous use of an absorption zone with a stripping zone to recover and/or separate hydrocarbons is described in U.S. Pat. Nos. 3,907,669 (Cl. 208–341); 4,009,097 (Cl. 208–392); 4,010,010 (Cl. 55–37); 3,072,604 (Cl. 208–341); 3,122,496 and 3,574,089 (both Cl. 208–101). These references show it is known to pass stripper bottoms liquid into an absorber as a lean liquid. The last of these references (U.S. Pat. No. 3,574,089) is pertinent for showing the commingling of the stripper overhead vapor, the absorber bottoms liquid and the feed to the separation zone followed by the passage of the resultant admixture into a vapor-liquid separator. The feed streams to the absorber and the stripper are removed from the separator in this reference. This method of operation is used commercially in the gas recovery units of fluidized catalytic cracking (FCC) units used in refining petroleum.

BRIEF SUMMARY OF THE INVENTION

The invention provides a novel process for the conversion of propane into high octane gasoline blending components which features a relatively simple method of recovering the product and of isolating the propane for recycling. One embodiment of the invention may be characterized as a hydrocarbon conversion process which comprises the steps of passing a feed stream comprising propane and a propane-rich recycle stream into a dehydrogenation zone and thereby forming a dehydrogenation zone effluent stream which comprises hydrogen, propane and propylene; passing the entire dehydrogenation zone effluent stream into a catalytic condensation zone and thereby forming a catalytic condensation zone effluent stream which comprises hydrogen, propane, $C_6$ hydrocarbons and $C_9$ hydrocarbons; passing the catalytic condensation zone effluent stream, a first absorber bottoms stream and a stripping column overhead stream into a vapor-liquid separation zone; passing a vapor stream comprising hydrogen and propane from the vapor-liquid separation zone into a first absorber and contacting the vapor stream with a first lean liquid hydrocarbon stream and thereby producing the first absorber bottoms stream and a first absorber vapor stream comprising hydrogen, $C_6$ hydrocarbons and propane; passing a liquid stream from the vapor-liquid separation zone into a stripping column and separating the liquid stream into a stripping column overhead stream comprising hydrogen and propane and a stripping column bottoms stream which comprises propane, $C_6$ hydrocarbons and $C_9$ hydrocarbons; passing a first portion of the stripping column bottoms stream into the first absorber as the first lean liquid hydrocarbon stream, and passing a second portion of the stripping column bottoms stream into a depropanizer column operated to effect the separation of the entering hydrocarbons into a depropanizer overhead stream comprising propane and a net depropanizer bottoms stream comprising $C_9$ hydrocarbons which is removed from the process as a product stream; removing a first portion of the first absorber vapor stream from the process as an off gas stream, contacting a second portion of the first absorber vapor stream with a second lean liquid which comprises a first portion of the depropanizer overhead stream to thereby form a second absorber bottoms stream comprising propane and $C_6$ hydrocarbons and a second absorber vapor stream; passing the second absorber bottoms stream into the stripping column; and, combining a second portion of the depropanizer overhead stream and the second absorber vapor stream with the feed stream as the propane-rich recycle stream which is passed into the dehydrogenation zone.

DESCRIPTION OF THE DRAWING

The Drawing is a schematic illustration of the preferred embodiment of the invention. Referring now to the Drawing, a stream of high purity propane enters the process through line 1 and is admixed with a recycle stream carried by line 2 which is rich in propane to form the feed stream to a dehydrogenation zone 4 which is carried by line 3. The propane which enters the dehydrogenation zone is contacted with a dehydrogenation catalyst at conditions effective to convert from about 30 to about 50 percent of the propane to propylene. This forms a dehydrogenation zone effluent stream carried by line 5 which comprises mainly hydrogen, propylene and propane and also contains some methane and $C_2$ hydrocarbons produced by the cracking of propane. Preferably, the entire dehydrogenation zone effluent stream is passed into a catalytic condensation zone 6 wherein the entering hydrocarbons are contacted with a solid catalyst under operating conditions selected to result in the conversion of substantially all of the propylene to $C_6$ and $C_9$ hydrocarbons.

The entire unseparated effluent of the catalytic condensation zone is carried by line 7 and comprises hydrogen, propane, $C_6$ and $C_9$ hydrocarbons. The effluent of the condensation zone is admixed with the stripper overhead vapor stream carried by line 23 and an absorber bottoms stream carried by line 20. The resultant mixed phase stream is passed into a vapor-liquid separator 9 through line 8. A vapor phase stream comprising hydrogen, light hydrocarbons ($C_1$ and $C_2$) and propane is removed from the separator 9 and passed through line 10 into the bottom portion of the absorber 12. This vapor stream rises upward countercurrent to a descending liquid stream which enters the upper portion of the absorber through line 19, with the residual unabsorbed hydrogen and propane exiting the top of the absorber as a first absorber vapor stream carried by line 13. A first portion of the first absorber vapor stream is removed from the process through line 14 as an off gas stream at a rate sufficient to remove the hydrogen and any $C_2$-hydrocarbons produced in a dehydrogenation zone. The vent gas stream may be passed through recovery facilities, such as a refrigerated condensation zone, to recover $C_6$ to $C_9$ hydrocarbons.

A liquid stream which comprises propane and $C_6$ and $C_9$ hydrocarbons is removed from the separator 9 in line 11 and passed into an upper portion of a stripping column or stripper 21. The stripper is operated under conditions which effect the fractionation of the entering hydrocarbon into a stripping column overhead vapor stream carried by line 23, which comprises propane and hydrogen, and a net stripping column bottoms liquid stream carried by line 24. The stripping column bottoms stream comprises the majority of the propane which enters the stripper 21 and also contains substantially all of the $C_6$ and $C_9$ hydrocarbons which enter the stripper. The stripping column bottoms stream is divided into two portions. A first portion enters the upper section of the absorber 12 through line 19 and a second portion is carried to a depropanizer 26 through line 25.

The depropanizer is designed and operated to separate the entering stripping column bottoms into a net bottoms stream removed from the process in line 27 as a net product stream which comprises $C_6$ and $C_9$ hydrocarbons suitable as gasoline blending components and a net overhead stream carried by line 28 which comprises propane and is substantially free of any other hydrocarbons. The net overhead stream of the depropanizer is divided into two portions, with a first liquid phase portion being passed into an upper section of a sponge absorber 16 through line 17 to act as a lean liquid utilized within the sponge absorber. This liquid passes downward through the absorber countercurrent to the rising second portion of the first absorber vapor stream carried by line 15. A desired result of this contacting operation is the production of a second absorber bottoms stream carried by line 22 which comprises propane and the $C_6$ and $C_9$ hydrocarbons which were originally present in the vapor stream entering the sponge absorber. This produces a second absorber vapor stream carried by line 18 which is substantially free of $C_6$ and $C_9$ hydrocarbons. The second absorber bottoms stream is passed into the stripper 21. The second absorber vapor stream is admixed with the remaining portion of the net depropanizer overhead stream and recycled to the dehydrogenation zone through line 2 as the previously referred to propane-rich recycle stream.

This description of the preferred embodiment of the invention is not intended to preclude from the scope of the inventive concept those other embodiments which are set out herein or which are the result of normal and expected modification of those embodiments. For clarity of presentation of the inventive concept, various pieces of apparatus and systems necessary for the practice of the invention, such as heat exchangers, control systems, fractionator internals, reboiling and overhead condensing systems, etc., have not been illustrated.

DETAILED DESCRIPTION

There has been a constantly increasing demand for high octane gasoline blending stocks. This is in part the result of the gradual phase down in the use of lead anti-knock compounds in gasoline. It also results from the steadily increasing number of motor vehicles which must be fueled with lead-free gasoline to prevent damage to the catalytic converters used in pollution reduction systems. For these and other reasons, it has become increasingly important to maximize both the quantity and the octane number of gasoline which is produced from available hydrocarbon feedstocks.

New facilities for the recovery of light hydrocarbons, such as propane and butane, which were previously wasted by flaring close to the site of their production are now coming on-stream in several Mideastern countries. There is presently no shortage of propane or butane on a world-wide basis, and the added production of propane and butane may result in there being an actual surplus of these light hydrocarbons.

It is an objective of the subject invention to provide a hydrocarbon conversion process for producing high octane motor fuel blending stocks. It is also an objective of the subject invention to provide an improved process for converting propane into gasoline. It is a further objective of the subject invention to provide a relatively simple and straight-forward process for the production of gasoline from propane.

The feed stream to the process is preferably a high purity stream of propane which contains less than 1.0 mole percent of any other hydrocarbon. The presence of propylene and/or various $C_4$ hydrocarbons in amounts above 1.0 mole percent each is, however, tolerable. The total concentration of hydrocarbons other than propane should never exceed 15 mole percent. The feed stream is preferably first admixed with a recycle stream, which comprises hydrogen and propane, and is then passed into a propane dehydrogenation zone. The feed stream and the recycle may also be passed into the dehydrogenation zone as separate unmixed streams.

The dehydrogenation zone will contain a reaction zone comprising one or more reactors and such auxiliary process equipment as is required for the operation of the reaction zone. The auxiliary equipment will include the customary heat exchangers, heaters, coolers, etc., found on many dehydrogenation process units. The effluent of the reaction zone may be cooled sufficiently to condense some of the hydrocarbons to thereby form a hydrogen-rich gas which is recirculated within the dehydrogenation zone to supply the desired hydrogen to hydrocarbon ratio within the reaction zone. It is preferred, however, that the entire effluent of the reaction zone is heat exchanged with the feed stream, further cooled and is then passed into the downstream catalytic condensation zone. That is, the effluent of the reaction zone is preferably not separated in any way and the total effluent of the reaction zone enters the catalytic condensation zone. This effluent stream will contain hydrogen, propane, propylene and any dehydrogenation by-products such as $C_1$ and $C_2$ hydrocarbons. The reaction zone of the dehydrogenation zone preferably comprises at least one radial flow reactor in which the catalyst gradually moves downward by gravity flow to allow the continuous replacement of used catalyst with catalyst having a higher activity. It is preferred that a multi-stage zone in which the reactants make at least two passes through a catalyst bed is employed. A detailed description of moving bed reactors of this type may be obtained by reference to U.S. Pat. Nos. 3,647,680; 3,652,231; 3,706,536; 3,785,963; 3,825,116; 3,839,196; 3,839,197; 3,854,887 and 3,856,662.

The particular dehydrogenation conditions employed within the reaction zone may vary depending on such factors as the catalyst activity, feed carbon number and the desired conversion. The conditions which may be employed for propane dehydrogenation include a temperature of from about 550° C. to 800° C., a pressure of from about 0.5 to about 20 atmospheres and a liquid hourly space velocity of about 0.5 to 20 $hr^{-1}$. The preferred propane dehydrogenation conditions are a temperature of from about 600° C. to 700° C., a pressure of 1.0 to 3.0 atmospheres, a liquid hourly space velocity of about 1 to 8 $hr^{-1}$ and a hydrogen to total hydrocarbon ratio between 1.0:1.0 to 5.0:1.0.

The preferred propane dehydrogenation catalyst is comprised of a platinum group component, a tin component and an alkali metal component with porous inorganic carrier material. Other catalytic compositions may be used within this zone if desired.

It is preferred that the porous carrier material is an absorptive high surface area support having a surface area of about 25 to about 500 $m^2/g$. The porous carrier material should be relatively refractory to the conditions utilized in the reaction zone and may be chosen from those carrier materials which have traditionally been utilized in dual-function hydrocarbon conversion catalysts. A porous carrier material may therefore be chosen from an activated carbon, coke or charcoal, silica or silica gel, clays and silicates including those synthetically prepared and naturally occurring which may or may not be acid-treated, as for example attapulgus clay, diatomaceous earth, kieselguhr, bauxite; refractory inorganic oxides such as alumina, titanium dioxide, zirconium dioxides, magnesia, silica-alumina, alumina-boria, etc.; crystalline aluminosilicates such as naturally occurring or synthetically prepared mordenite or a combination of one or more of these materials. The preferred porous carrier material is a refractory inorganic oxide with the best results being obtained with an alumina carrier material. The crystalline aluminas, such as gamma alumina, give the best results. In general, the preferred catalysts will have a gamma alumina carrier which is in the form of spherical particles having a relatively small diameter on the order of about 1/16-inch.

The preferred alumina carrier material may be prepared in any suitable manner. For example, the alumina carrier may be prepared by adding a suitable alkaline reagent, such as ammonium hydroxide to a salt of alumina such as aluminum chloride in an amount to form an aluminum hydroxide gel which upon drying and calcining, is converted to alumina. It is particularly preferred that alumina spheres are manufactured by the well-known oil drop method which comprises forming an alumina hydrosol by the techniques taught in the art, and preferably by reacting aluminum metal with hydrochloric acid, and combining the hydrosol with a suitable gelling agent. The resultant mixture is dropped into an oil bath maintained at elevated temperatures. The droplets remain in the oil bath until they set and form hydrogel spheres. The spheres are then continuously withdrawn from the oil bath and are normally subjected to specific aging treatments in oil and an ammoniacal solution to further improve their physical characteristics. The resulting pellets are then washed and dried at relatively low temperatures of about 150° C., to about 200° C. and calcined at a temperature of about 450° C. to about 700° C. for a period of about 1 to about 20 hours. See the teachings of U.S. Pat. No. 2,620,314 for additional details on the preparation of the base material by the oil dropping method.

The preferred dehydrogenation catalyst also contains a platinum group component. Of the platinum group metals, which include palladium, rhodium, ruthenium, osmium and iridium, the use of platinum is preferred. The platinum group component may exist within the final catalyst composite as a compound such as an oxide, sulfide, halide, oxysulfide, etc., or as an elemental metal or in combination with one or more other ingredients of the catalyst. It is believed that best results are obtained when substantially all the platinum group component exists in the elemental state. The platinum group component generally comprises from about 0.01 to about 2 wt.% of the final catalytic composite, calculated on an elemental basis. It is preferred that the platinum content of the catalyst is between about 0.1 and 1.0 wt.%. The preferred platinum group component is platinum, with palladium being the next preferred metal. The platinum group component may be incorporated into the catalytic composite in any suitable manner such as by coprecipitation or cogellation with the preferred carrier material, or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinic or chloropalladic acid. An acid such as hydrogen chloride is generally added to the impregnation solution to aid in the distribution of the platinum group component throughout the carrier material.

The tin component of the preferred catalyst should constitute about 0.01 to about 5 wt.% of the final composite, calculated on an elemental basis, although substantially higher amounts of tin may be utilized in some cases. Best results are often obtained with about 0.1 to about 1 wt.% tin. It is preferred that the atomic ratio of tin to platinum is between 1:1 to about 6:1. The tin component may be incorporated into the catalytic composite in any suitable manner known to effectively disperse this component in a very uniform manner throughout the carrier material. Thus, the component may be added to the carrier by coprecipitation. A preferred method of incorporating the tin component involves coprecipitating it during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into the oil bath as previously described. The tin component may also be added through the utilization of a soluble, decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

The preferred propane dehydrogenation catalyst contains less than 0.5 wt.% halogen and preferably less than 0.1 wt.% halogen. Residual amounts of any halogen, such as chlorine, at or below this concentration may be tolerated. The preferred catalyst does however contain an alkali metal component chosen from cesium, rubidium, potassium, sodium, and lithium. The preferred alkali metal is lithium. The concentration of the alkali metal may range from between 0.1 and 3.5 wt.% but is preferably between 0.2 and about 1.5 wt.% calculated on an elemental basis.

As previously mentioned, it is preferred that the entire effluent of the propane dehydrogenation zone is passed into the catalytic condensation zone. This zone is similar in function to other zones which are referred to as oligomerization zones. The catalytic condensation zone may take many forms depending on such variables as the catalyst which is employed within this zone. For instance, U.S. Pat. Nos. 3,932,553 and 3,997,621 describe processes in which boron trifluoride is utilized as a catalyst. Both of these catalytic systems utilize a minor amount of an additive to control the extent to which the reaction proceeds. In both of these references, the catalyst system appears to be homogeneous. Heterogeneous catalytic systems for the production of higher molecular weight olefins by the oligomerization or dimerization of light olefins are described in U.S. Pat. Nos. 3,906,053; 3,916,019; 3,959,400; 3,981,940 and 3,981,941. As may be expected from the large number of processes, the conditions employed within the reaction zone may vary widely. For instance, the just cited references specify that the reaction may be performed at temperatures ranging from −50° C. to 250° C. and at a pressure ranging from about 1.3 atmospheres gauge to approximately 100 atmospheres gauge.

The preferred catalyst for use in the catalytic condensation zone is an SPA (solid phosphoric acid) type catalyst. As used herein, the term "SPA catalyst" is intended to indicate a solid catalyst which contains as one of its principal ingredients an acid of phosphorus such as an ortho-, pyro- or tetra-phosphoric acid. The catalyst is normally formed by mixing the acid of phosphorus with a siliceous, solid carrier to form a wet paste. This paste may be calcined and then crushed to yield catalyst particles, or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives, such as mineral talc, fullers earth and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. Variations from this such as a lower phosphoric acid content are however possible. Further details as to the composition and production of SPA catalysts may be obtained from U.S. Pat. Nos. 3,050,472; 3,050,473 and 3,132,109 and from other references.

The catalyst is preferably disposed in fixed beds within the catalytic condensation zone. Either a tubular or chamber-type reactor structure may be used. In a tubular reactor, the catalyst is placed in relatively small diameter tubes which are surrounded by a water jacket to remove the heat liberated by the exothermic reaction. Steam generated in this manner can be used to preheat the feed. In a chamber-type reactor, the reactants flow through a series of large diameter catalyst beds. The temperature of the reactants is controlled by recycling relatively inert hydrocarbons which act as a heat sink or by the use of a quench between vertically stacked catalyst beds. The quench material is the same as that used as the recycle stream, and both methods of temperature control may be used simultaneously. The different catalyst beds are preferably contained within a single, cylindrical, vertically oriented vessel, and the feed stream preferably enters the top of the reactor. A chamber-type reactor containing about five catalyst beds is preferred.

The catalytic condensation zone is maintained at conditions which may vary widely due to the previously listed variables. A broad range of suitable pressures is from about 15 psig. to about 1200 psig., with a preferred pressure range for an SPA catalyst being from 400 to 1000 psig. The temperature maintained in this zone with the preferred SPA catalyst may vary from about 120° C. to about 260° C. Steam or water may be fed into the reactor to maintain the desired water content in the preferred catalyst. It is preferred that the catalytic condensation zone contains no fractionation columns, vapor-liquid separators or other means to separate or purify the effluent stream.

In the preferred embodiment, an SPA catalyst is utilized in a chamber-type reactor to form an effluent containing $C_6$ and $C_9$ hydrocarbons having boiling points within a gasoline boiling point range of about 43° C. to about 215° C. as determined by the appropriate ASTM distillation method. Preferably, the feed stream is first heat exchanged with the reactor effluent, further heated and then passed into the top of the reactor. Additional amounts of a propane/hydrogen coolant similar in composition to the recycle stream are preferably added between each of the catalyst beds. As previously mentioned, the effluent of the catalytic condensation zone will also contain relatively unreactive propane and the hydrogen which was produced in the dehydrogenation zone.

The effluent of the catalytic condensation zone is then passed directly into a separation zone wherein the gasoline boiling range components of the effluent stream are concentrated into a product stream. This separation zone may take other forms than the preferred system shown in the Drawing. For instance, the effluent stream could be separated through the use of a more straight-forward series of fractionation columns which produce separate bottoms streams of gasoline boiling range components and propane respectively. Another possible variation in the separation zone is the use of adsorption to separate all or some of the components. For instance, a zeolitic adsorbent could be used to recover propane from a process stream which is a mixture of propane and hydrogen. The other functions of the separation zone are to also produce a recycle stream, which contains hydrogen and most of the propane in the effluent stream, and a hydrogen-rich vent gas stream. The recycle stream should be essentially free of $C_6$ hydrocarbons. The vent gas stream is required to provide a means of eliminating from the process the hydrogen and any light hydrocarbons produced in the dehydrogenation zone. As used herein, any reference to a stream as being "rich" in any chemical compound or group of compounds is intended to specify that at least 55 mole percent of the stream is the specified compound or group of compounds.

One broad embodiment of the invention may be characterized as a hydrocarbon conversion process which comprises the steps of passing a feed stream comprising propane and a hereinafter characterized recycle stream into a dehydrogenation zone operated at propane dehydrogenation conditions and thereby forming a dehydrogenation zone effluent stream comprising hydrogen, propane and propylene; passing the entire dehydrogenation zone effluent stream into a catalytic condensation zone operated at conditions which effect the conversion of propylene into $C_9$ hydrocarbons and thereby forming a catalytic condensation zone effluent stream which comprises hydrogen, propane and $C_9$ hydrocarbons; and separating the catalytic condensation zone effluent stream into a vent gas stream comprising hydrogen, the said recycle stream, which comprises hydrogen and propane, and a product stream which comprises $C_9$ hydrocarbons.

The preferred form of the separation zone used to recover the product is shown in the Drawing. It is preferred that the catalytic condensation zone effluent stream is first admixed with the stripping column net overhead vapor stream and then passed through a cooler which condenses much of the propane in the resultant admixture. The absorber bottoms stream is mixed into this mixed-phase stream and then the admixture of all three streams is passed into the vapor-liquid separator. This is preferably a vertical vessel of suitable size and construction to allow the entering fluids to separate into a vapor stream comprising mainly hydrogen and propane and a liquid stream comprising propane and $C_6$ and $C_9$ hydrocarbons. The vapor stream will also contain small amounts of $C_6$ and $C_9$ hydrocarbons and the liquid stream will have some hydrogen dissolved in it. Assuming the desired entering fluids composition, the vapor-liquid separator may be operated at a pressure of about 525 psig. and a temperature of approximately 50° C.

The vapor stream which is removed from the vapor-liquid separator is preferably passed into the lower portion of a first absorber. This absorber is preferably a vertical trayed column having about 30 trays. The vapor stream enters close to the bottom of the column and rises upward countercurrent to a descending liquid which flows across the trays. The vapor stream may be at a temperature of about 50° C. when it enters this absorber, which may be operated at a pressure of about 500 psig. and an average temperature of approximately 40° C. This first absorber is preferably operated at conditions under which most of the entering propane is concentrated into a first absorber bottoms stream with less than 5.0 mole percent of the entering propane being contained in the absorber vapor stream which exits the top of the column. The absorber bottoms stream should contain substantially all of the $C_6$ and $C_9$ hydrocarbons which enter the absorber, but a small amount of $C_6$ hydrocarbons will be present in the absorber vapor stream due to the lean liquid containing $C_6$ and $C_9$ hydrocarbons. As used herein, the term "substantially all" is intended to indicate at least 95 mole percent of the specified chemical compound. The liquid-phase first absorber bottoms stream is passed into the vapor-liquid separator. The function of the absorber is to remove substantially all of the $C_6$ and $C_9$ hydrocarbons from the entering vapor stream. The absorber vapor stream is passed into a second absorber.

The liquid stream which is removed from the vapor-liquid separator is preferably passed into a reboiled stripping column. This stripping column or stripper is preferably a single vertical trayed column having about 30 trays. The liquid stream is preferably fed onto an upper tray of this column, from which it passes downward from tray to tray countercurrent to rising vapors. The function of the stripping column is to remove the majority of the entering propane from the descending liquid and to produce a stripping column bottoms stream which contains over 85 mole percent of the entering $C_6$ and $C_9$ hydrocarbons. The stripping column bottoms stream will also contain a sizable amount of propane and may be a propane-rich stream depending on the recycle rates employed in the process. Representative operating conditions for the bottom of the stripping column include a bottoms liquid temperature of approximately 100° C. and a pressure of about 520 psig. The stripping column overhead vapor stream will be rich in propane and contain a small amount of hydrogen and $C_6$ hydrocarbons. It is recycled into the vapor-liquid separator. The stripping column bottoms stream is divided into two portions. A first portion is passed into the top of the first absorber to function as the lean liquid hydrocarbon required in the absorber. The second portion of the stripping column bottoms stream is passed into a product depropanizer column.

A second liquid stream, the second absorber bottoms described below, is preferably also passed into the stripping column. This second liquid stream may be admixed with the liquid stream from the vapor-liquid separator before passage into the stripping column. The two liquid streams may also be passed into the stripping column at different points which correspond to their respective compositions. It is expected the second liquid stream will normally have a higher propane concentration than the vapor-liquid separator liquid stream and therefore would be fed onto the top tray of the stripping column somewhat above the vapor-liquid separator liquid stream.

The portion of the stripping column bottoms liquid stream which is not used as lean absorption liquid in the first absorber is passed into a product depropanizer. This is preferably a single trayed column which may have about 36 trays. This reboiled column has an external reflux system to produce a net overhead stream which is substantially pure propane. That is, this net overhead stream should contain at least 99 mole percent propane and be substantially free of $C_6$ hydrocarbons. The net bottoms stream of the depropanizer is the gasoline blending stock product of the process. This bottoms stream will therefore contain substantially all $C_6$ and $C_9$ hydrocarbons which enter the depropanizer. Any other relatively heavy hydrocarbons, such as $C_5$ or $C_8$ hydrocarbons, produced in the catalytic condensation zone will be concentrated into this bottoms stream. The depropanizer bottoms stream should contain less than 1.0 mole percent propane. Representative operating conditions for the depropanizer column include a bottoms liquid temperature of approximately 200° C. and a pressure of about 260 psig.

At least a portion of the vapor stream of the first absorber is passed into a second absorber which is commonly referred to as a sponge absorber. A vertical column having about 20 trays is sufficient. The function of this second absorber is to remove $C_6$ and $C_9$ hydrocarbons from the entering vapor stream. This vapor stream contains the hydrogen which is to be recycled to the high temperature propane dehydrogenation reactor. $C_6$ and $C_9$ hydrocarbons which enter the dehydrogenation reactor tend to form detrimental carbonaceous deposits on the dehydrogenation catalyst which adversely affect the activity of the catalyst. It is therefore undesirable to have $C_6$ hydrocarbons recycled to the dehydrogenation zone from the first absorber vapor stream. The lean hydrocarbon liquid fed to the second absorber is a portion of the depropanizer column overhead stream, which is high purity propane. The sponge absorber is operated at conditions which maintain liquid-phase propane within the absorber. A representative set of operating conditions include a temperature near 40° C. and a pressure of about 400 psig. as measured as the top tray of the absorber. The lean liquid will descend through the absorber collecting $C_6$ and $C_9$ hydrocarbons from the rising vapor to thereby form the second absorber bottoms stream, a liquid stream which is rich in propane and contains substantially all of the $C_6$ and $C_9$ hydrocarbons which enter the second absorber. The second absorber bottoms stream is passed into the stripping column as previously described.

The second absorber vapor stream is rich in hydrogen and may contain over 85 mole percent hydrogen. At least a portion of this vapor stream is recycled to the dehydrogenation zone to provide the hydrogen which is circulated through the reactor. It is preferred that this vapor stream is admixed with the remaining portion of the depropanizer overhead stream, which is the propane recycled in the process, to form a single recycle stream which is then admixed with the feed stream. However, each stream may also be separately admixed with the feed stream.

An off gas stream is removed from the process to remove the hydrogen produced in the dehydrogenation zone. This stream may be a portion of either the first or the second absorber vapor streams. Where the vent gas stream is removed will depend on design considerations which may differ between individual units. Removing a portion of the second absorber vapor may be advantageous when a higher hydrogen purity is desired. Removing a portion of the first absorber vapor stream has the advantage of reducing the required size of the second absorber. This therefore leads to two separate limited embodiments of the invention. One of these limited embodiments may be characerized as a hydrocarbon conversion process which comprises the steps of passing a feed stream comprising propane and a hereinafter characterized recycle stream into a dehydrogenation zone operated at propane dehydrogenation conditions and thereby forming a dehydrogenation zone effluent stream comprising hydrogen, propane and propylene; passing the entire dehydrogenation zone effluent stream into a catalytic condensation zone operated at conditions which effect the conversion of propylene into $C_9$ hydrocarbons and thereby forming a catalytic condensation zone effluent stream which comprises hydrogen, propane, $C_6$ hydrocarbons and $C_9$ hydrocarbons; passing the catalytic condensation zone effluent stream, a first absorber bottoms stream and a stripping column overhead stream into a vapor-liquid separation zone; passing a vapor stream comprising hydrogen and propane and which is withdrawn from the vapor-liquid separation zone into a first absorber and contacting the vapor stream at absorption-promoting conditions with a first lean liquid hydrocarbon stream comprising $C_6$ and $C_9$ hydrocarbons and thereby producing the first absorber bottoms stream, which comprises propane and $C_9$ hydrocarbons, and a first absorber vapor stream comprising hydrogen, propane and $C_6$ hydrocarbons; passing a liquid stream comprising $C_6$ and $C_9$ hydrocarbons and which is withdrawn from the vapor-liquid separation zone into a stripping column operated at conditions which effect the separation of the liquid stream into a stripping column overhead stream comprising hydrogen and propane and a stripping column bottoms stream which comprises propane, $C_6$ hydrocarbons and $C_9$ hydrocarbons; passing a first portion of the stripping column bottoms stream into the first absorber as the previously specified first lean liquid hydrocarbon stream, and passing a second portion of the stripping column bottoms stream into a depropanizer column operated at conditions which effect the separation of the entering hydrocarbons into a depropanizer overhead stream comprising propane and a net depropanizer bottoms stream removed from the process as a product stream which comprises $C_6$ and $C_9$ hydrocarbons and is substantially free of propane; passing the first absorber vapor stream into a second absorber and contacting the first absorber vapor stream with a second lean liquid hydrocarbon stream at absorption-promoting conditions and thereby producing a second absorber bottoms stream, which comprises propane and $C_6$ hydrocarbons, and a second absorber vapor stream which comprises propane; passing the second absorber bottoms stream into the stripping column; removing a first portion of the second absorber vapor stream from the process as an off gas stream; and passing a first portion of the depropanizer overhead stream into the second absorber as the previously specified second lean liquid hydrocarbon stream, and combining a second portion of the depropanizer overhead stream and a second portion of the second absorber vapor stream with the feed stream as the previously referred to recycle stream.

We claim as our invention:

1. A hydrocarbon conversion process which comprises the steps of:
   (a) passing a feed stream comprising propane and a hereinafter characterized recycle stream into a dehydrogenation zone operated at propane dehydrogenation conditions and thereby forming a dehydrogenation zone effluent stream comprising hydrogen, propane and propylene;
   (b) passing the entire dehydrogenation zone effluent stream into a catalytic condensation zone operated at conditions which effect the conversion of propylene into $C_9$ hydrocarbons and thereby forming a catalytic condensation zone effluent stream which comprises hydrogen, propane, $C_6$ hydrocarbons and $C_9$ hydrocarbons;
   (c) passing the catalytic condensation zone effluent stream, a first absorber bottoms stream and a stripping column overhead stream into a vapor-liquid separation zone;

(d) passing a vapor stream comprising hydrogen and propane and which is withdrawn from the vapor-liquid separation zone into a first absorber and contacting the vapor stream at absorption-promoting conditions with a first lean liquid hydrocarbon stream comprising $C_6$ and $C_9$ hydrocarbons and thereby producing the first absorber bottoms stream, which comprises propane and $C_9$ hydrocarbons, and a first absorber vapor stream comprising hydrogen, propane and $C_6$ hydrocarbons;

(e) passing a liquid stream comprising $C_6$ and $C_9$ hydrocarbons and which is withdrawn from the vapor-liquid separation zone into a stripping column operated at conditions which effect the separation of the liquid stream into a stripping column overhead stream comprising hydrogen and propane and a stripping column bottoms stream which comprises propane, $C_6$ hydrocarbons and $C_9$ hydrocarbons;

(f) passing a first portion of the stripping column bottoms stream into the first absorber as the previously specified first lean liquid hydrocarbon stream, and passing a second portion of the stripping column bottoms stream into a depropanizer column operated at conditions which effect the separation of the entering hydrocarbons into a depropanizer overhead stream comprising propane and a net depropanizer bottoms stream removed from the process as a product stream which comprises $C_6$ and $C_9$ hydrocarbons and is substantially free of propane;

(g) removing a first portion of the first absorber vapor stream from the process as an off gas stream, and passing a second portion of the first absorber vapor stream into a second absorber and contacting the second portion of the first absorber vapor stream with a second lean liquid hydrocarbon stream at absorption-promoting conditions and thereby producing a second absorber bottoms stream, which comprises propane and a second adsorber vapor stream;

(h) passing the second absorber bottoms stream into the stripping column; and, (i) passing a first portion of the depropanizer overhead stream into the second absorber as the previously specified second lean liquid hydrocarbon stream, and combining a second portion of the depropanizer overhead stream and the second absorber vapor stream with the feed stream as the previously referred to recycle stream of step (a).

2. The process of claim 1 further characterized in that the stripping column overhead stream is rich in hydrogen and in that the second absorber vapor stream comprises hydrogen and is substantially free of $C_6$ hydrocarbons.

3. A hydrocarbon conversion process which comprises the steps of:

(a) passing a feed stream comprising propane and a hereinafter characterized recycle stream into a dehydrogenation zone operated at propane dehydrogenation conditions and thereby forming a dehydrogenation zone effluent stream comprising hydrogen, propane and propylene;

(b) passing the entire dehydrogenation zone effluent stream into a catalytic condensation zone operated at conditions which effect the conversion of propylene into $C_9$ hydrocarbons and thereby forming a catalytic condensation zone effluent stream which comprises hydrogen, propane, $C_6$ hydrocarbons and $C_9$ hydrocarbons;

(c) passing the catalytic condensation zone effluent stream, a first absorber bottoms stream and a stripping column overhead stream into a vapor-liquid separation zone;

(d) passing a vapor stream comprising hydrogen and propane and which is withdrawn from the vapor-liquid separation zone into a first absorber and contacting the vapor stream at absorption-promoting conditions with a first lean liquid hydrocarbon stream comprising $C_6$ and $C_9$ hydrocarbons and thereby producing the first absorber bottoms stream, which comprises propane and $C_9$ hydrocarbons, and a first absorber vapor stream comprising hydrogen, propane and $C_6$ hydrocarbons;

(e) passing a liquid stream comprising $C_6$ and $C_9$ hydrocarbons and which is withdrawn from the vapor-liquid separation zone into a stripping column operated at conditions which effect the separation of the liquid stream into a stripping column overhead stream comprising hydrogen and propane and a stripping column bottoms stream which comprises propane, $C_6$ hydrocarbons and $C_9$ hydrocarbons;

(f) passing a first portion of the stripping column bottoms stream into the first absorber as the previously specified first lean liquid hydrocarbon stream, and passing a second portion of the stripping column bottoms stream into a depropanizer column operated at conditions which effect the separation of the entering hydrocarbons into a depropanizer overhead stream comprising propane and a net depropanizer bottoms stream removed from the process as a product stream which comprises $C_6$ and $C_9$ hydrocarbons and is substantially free of propane;

(g) passing the first absorber vapor stream into a second absorber and contacting the first absorber vapor stream with a second lean liquid hydrocarbon stream at absorption-promoting conditions and thereby producing a second absorber bottoms stream, which comprises propane and $C_6$ hydrocarbons, and a second absorber vapor stream which comprises propane;

(h) passing the second absorber bottoms stream into the stripping column;

(i) removing a first portion of the second absorber vapor stream from the process as an off gas stream; and, (j) passing a first portion of the depropanizer overhead stream into the second absorber as the previously specified second lean liquid hydrocarbon stream, and combining a second portion of the depropanizer overhead stream and a second portion of the second absorber vapor stream with the feed stream as the previously referred to recycle stream of step (a).

4. The process of claim 3 further characterized in that the stripping column overhead stream is rich in hydrogen and in that the second absorber vapor stream comprises hydrogen and is substantially free of $C_6$ hydrocarbons.

* * * * *